United States Patent [19]

Yehuda

[11] Patent Number: 5,288,755
[45] Date of Patent: * Feb. 22, 1994

[54] PHYSIOLOGICALLY ACTIVE AND NUTRITIONAL COMPOSITION

[75] Inventor: Shlomo Yehuda, Tel Aviv, Israel

[73] Assignee: Bar Ilan University, Ramat Gan, Israel

[ * ] Notice: The portion of the term of this patent subsequent to Jul. 25, 2006 has been disclaimed.

[21] Appl. No.: 820,562

[22] Filed: Jan. 14, 1992

Related U.S. Application Data

[60] Division of Ser. No. 376,289, Jul. 6, 1989, Pat. No. 5,120,763, which is a continuation-in-part of Ser. No. 120,830, Nov. 16, 1987, Pat. No. 4,851,431, and a continuation-in-part of Ser. No. 263,548, Oct. 27, 1988, abandoned, and a continuation-in-part of Ser. No. 359,562, Jun. 1, 1989, abandoned.

[51] Int. Cl.$^5$ ...................... A61K 31/22; A61K 31/20
[52] U.S. Cl. ..................................... 514/549; 514/558
[58] Field of Search ............... 514/549, 522, 560, 557, 514/168, 52, 251, 276, 345, 356, 392, 458, 474, 681, 725, 558; 424/601, 630, 639, 643, 655, 682

[56] References Cited

U.S. PATENT DOCUMENTS

| Re. 31,836 | 2/1985 | Horrobin | 514/474 |
|---|---|---|---|
| 3,011,949 | 12/1961 | Bilotti | 424/439 |
| 3,882,256 | 5/1975 | De Boer | 426/583 |
| 3,962,416 | 6/1976 | Katzen | 424/19 |
| 4,058,594 | 11/1977 | Williams | 424/37 |
| 4,097,604 | 6/1978 | Thiele | 424/318 |
| 4,273,763 | 6/1981 | Horrobin | 424/145 |
| 4,302,447 | 11/1981 | Horrobin | 424/145 |
| 4,328,243 | 5/1982 | Horrobin et al. | 424/301 |
| 4,370,315 | 1/1983 | Greff et al. | 424/94 |
| 4,386,072 | 5/1983 | Horrobin et al. | 424/127 |
| 4,393,049 | 7/1983 | Horrobin | 424/145 |
| 4,415,554 | 11/1983 | Horrobin | 424/145 |
| 4,513,008 | 4/1985 | Revici et al. | 514/560 |
| 4,668,704 | 5/1987 | Hollander et al. | 514/560 |
| 4,670,468 | 6/1989 | Hollander et al. | 514/560 |
| 4,810,497 | 3/1989 | Horrobin | 514/560 |
| 4,851,431 | 7/1989 | Yehuda | 514/560 |
| 4,996,233 | 2/1991 | Horrobin | 514/560 |

FOREIGN PATENT DOCUMENTS

| 0037175 | 10/1981 | European Pat. Off. . |
|---|---|---|
| 0071357 | 2/1983 | European Pat. Off. . |
| 0181689 | 5/1986 | European Pat. Off. . |
| 0234733 | 9/1987 | European Pat. Off. . |
| 2134782 | 8/1984 | United Kingdom . |

OTHER PUBLICATIONS

Horrobin, D. F., Medical Hypothesis, 6:469–486 (1980).
Modern Drug Encyclopedia, 1961, 8th Edition, ed. H. D. Fein, The Reuben H. Donnelly Corp., N.Y., p. 663, "Lenic".

(List continued on next page.)

*Primary Examiner*—Frederick E. Waddell
*Assistant Examiner*—Raymond J. Henley, III
*Attorney, Agent, or Firm*—Darby & Darby

[57] ABSTRACT

A composition of matter which consists of (a) from about 13.0 to about 27.5% by weight of at least one compound selected from the group consisting of linolenic acid and derivatives thereof, calculated as the free acid, said derivatives of linolenic acid being both physiologically hydrolyzable and pharmacologically acceptable, and (b) about 87.0 to about 72.5% by weight of at least one compound selected from the group consisting of linoleic acid and derivatives thereof, calculated as the free acid, said derivatives of linoleic acid being both physiologically hydrolyzable and pharmacologically acceptable is utilized in a nutritional composition, in absence of an oily carrier or diluent which comprises at least one member of the group consisting of $C_{8-18}$ saturated fatty acids, oleic acid and derivatives of these acids, in order to induce in a mammal (including humans) at least one physiological effect selected from memory enhancement, analgesia, sleep regulation and inhibition of the symptoms of senility. The invention also relates to a method for treating a mammal with the composition for the purpose of inducing such a physiological effect therein.

9 Claims, No Drawings

OTHER PUBLICATIONS

Moncada et al., Chapter 28—Prostaglandis, Prostacyclin, Thromboxane $A_2$, and Leucotrienes.

Goodman & Gilman's, The Pharmacological Basis of Therapeutics, 7th Ed., McMillan Publishing Co., pp. 1546, 1548 (1985).

Brinkman et al., Chem. Abst., vol. 103, 1985, No. 212685x.

Brinkman et al., Chem. Abst., vol. 96, 1982, No. 210912g.

Innis, Sheila M., "Effect of Total Parenteral Nutrition with Linoleic Acid-Rich Emuslions on Tissue ω6 and ω3 Fatty Acids in the Rat", LIPIDS, 21(2):132-8 (1986).

Rahm, J. J., et al., "Effect of Linoleic Acid Upon the Metabolism of Linoleic Acid", J. Nutrition, 84(1):15-19 (1964).

Ciangherotti, S., et al., "Significato Nutrizionale dell-'acido linolenico", Riv. Ital. Sostanze Grasse, 61(5):293-6 (1984).

Mohrhauer et al., "Effect of Linolenic Acid Upon the Metabolism of Linolenic Acid", J. Nutrition, 81(1):67-74 (1963).

Budowski et al., "Alpha-Linolenic Acid as a Regulator of the Metabolism of Arachidonic Acid: Dietary Implications of the Ratio, n-6:n-3 Fatty Acids", Proceedings of the Nutrition Society, 44:221-229 (1985).

Chem. Abstracts, 47:10644 (1985).

Carlson et al., "High Fat Diets Varying in Ratios of Polyunsaturated to Saturated Fatty Acid and Linolenic Acid: A comparison of Rat Neural and Red Cell Membrane Phospholipids", J. Nutrition, 116(5):718-25 (1986).

Marx, Science, vol. 250, pp. 1509-1510 (1990).

Thompson et al., New England Journal of Medicine, 323(7), 1990, pp. 445-448.

Gauthier et al., New England Journal of Medicine, 322, pp. 1272-1276 (1990).

Sigma Catalog, 1990, E7134, L1376, L2376, L2378.

Teri et al., Journal of Gerontology Psychological Sciences, 45(2), pp. 58-63 (1990).

Applegate et al., New England Journal of Medicine, 322:1207-1214 (1990).

Berg et al., Mt. Sinai Journal of Medicine, 55(1), pp. 87-94 (1988).

Burns et al., Int. Psychogeriatrics, 2(1), pp. 25-26 (1990).

PHYSIOLOGICALLY ACTIVE AND NUTRITIONAL COMPOSITION

This is a division of application Ser. No. 07/376,289, filed Jul. 6, 1989 now U.S. Pat. No. 5,120,763, which is a continuation-in-part of U.S. application Ser. No. 07/120,830, filed Nov. 16, 1987 entitled "Physiologically Active and Nutritional Composition" now U.S. Pat. No. 4,851,431; of U.S. application Ser. No. 263,548, filed Oct. 27, 1988 entitled "Method for Treating Alzheimer's Disease and Related Dementias" now abandoned; and of U.S. application Ser. No. 07/359,562, filed Jun. 1, 1989 entitled "Method for Treating Epilepsy," now abandoned.

FIELD OF THE INVENTION

The present invention relates to a composition of matter having useful physiological and nutritional activity and applications, and to a method for inducing memory enhancement, analgesia, sleep regulation and inhibition of the symptoms of senility, for treating Alzheimer's disease and related dementias, and for treating epilepsy. The present application is filed as a continuation-in-part of U.S. application Ser. No. 07/120,830 filed Nov. 15, 1987 entitled "Physiologically Active and Nutritional Composition"; of U.S. application Ser. No. 263,548 filed Oct. 27, 1988 entitled "Method for Treating Alzheimer's Disease and Related Dementias"; and of U.S. application Ser. No. 07/359,562 filed Jun. 1, 1989 entitled "Method for Treating Epilepsy".

BACKGROUND OF THE INVENTION

It has been recognized for many years that the mammalian body requires for its nutrition relatively large amounts of fats, carbohydrates and proteins, and by contrast relatively small amounts of vitamins and minerals; lack of these latter classes of substances has been held to be accountable for the absence of general good health as well as the incidence of various specific bodily ailments. Vitamins and minerals are normally ingested or otherwise produced from the mammalian diet, but to a certain extent may also or alternatively be produced in the body. For various reasons which may be related to the source of supply or the manufacturing processes used, foods are sometimes lacking or dificient in vitamins and/or minerals, and even where vitamins are synthesized in the body, such a process may not produce the amount required. Over a period of time there has therefore grown up the use of food supplements, or nutritional compositions, to supply the ingredients of this nature required by the body, but which are either not produced therein in sufficient amounts, or are not supplied thereto by the regular diet of the subject in sufficient amounts.

Nutritional compositions are not at the present time, however, restricted merely to a content of vitamins and minerals, as the sole active ingredients. Other materias which are intermediate in metabolic processes and which it is though may not be produced in sufficient amounts (at least in subjects with abnormal metabolism) may also be present in nutritional compositions. Examples of such other materials are unsaturated fatty acids, such as linoleic acid, gamma-linolenic acid, dihomogamma-linolenic acid arachidonic and eicosapentaenoic aoids, as well as physiologically compatible derivatives thereof, such as salts, esters and amides of such acids, which may be metabolized in the body to prostaglandins. Prostaglandins are an important group of local hormones which act within the body tissues in which they are synthesized, in roles which are not entirely understood, though they may act at least to lower blood pressure, and to induce smooth muscle to contract.

Horrobin, in Med. Hypotheses 6: 469–486 (1980), has also proposed that a metabolic abnormality in the synthesis of certain prostaglandins is responsible for allowing an initial cancer cell to divide indefinitely, the abnormality being in particular, inhibition of the enzyme delta-6-desaturase which converts essential unsaturated fatty acids in normal cells to prostaglandins. He has also proposed pharmaceutical compositions (see e.g. EP 0037175 published Oct. 7, 1981 and prior patent applications referred to therein, the contents of which are to be regarded as incorporated herein by reference) comprising certain unsaturated fatty acids together with other ingredients which enhance formation in the body of essential prostaglandins and therefore bypass the metabolic abnormality referred to above.

In general, fatty acids in combined form are present in animal and vegetable fats and oils, but vegetable oils such as corn, cottonseed and soya oils contain in general a higher ratio of unsaturated to saturated acids, than do animal fats. A higher proportion of polyunsaturated fatty acids (such as linoleic and linolenic acids) in the diet apparently tends to reduce the incidence of heart disease, although whether this is due to a positive effect of the polyunsaturated compounds themselves, rather than to an intake of a correspondingly lower proportion of saturated compounds (and of cholesterol which is also present in animal fats), or to a lower fat intake overall, remains uncertain.

Senile dementia of Alzheimer's type (more commonly known as "Alzheimer's disease") appears to be the most widespread neuropsychiatrio disease and is becoming increasingly prevalent with the general aging of the population. It is not, however, confined to the elderly, as this term is generally understood. To the best of the inventor's knowledge, no satisfactory treatment for this type of dementia or for related dementias has yet been evolved.

The term "epilepsy" denotes a group of central nervous system disorders characterized by transitory episodes of abnormal motor, sensory, autonomic or psychic phenomena, and are almost always correlated with abnormal and excessive discharges in the encephalogram. Most known useful antiepileptic agents are either barbiturates or are structurally related thereto, or are benzodiazepines, dibenzoazepines, or lipide or lipid-like compounds containing phosphorus and/or nitrogen. Valproic acid ($Pr_2CHCOOH$) and its derivatives are also useful in this respect. However, to the inventor's knowledge, it has not hitherto been proposed to use polyunsaturated unbranched long-chain carboxylic acids, containing only C, H and O, as antiepileptic compounds.

It has now been surprisingly found in accordance with the present invention, that a combination of two naturally occurring polyunsaturated acids within a certain range of proportions, produces certain beneficial effects in the human and animal body, including memory enhancement, analgesia, sleep regulation and inhibition of the symptoms of senility; and may also be used in a method of treatment for Alzheimer's disease and related dementias, and epilepsy, which method relieves at least certain symptoms of such diseases.

Experiments carried out by the inventor support the belief that it is the combination of these acids themselves in particular proportions which is the active factor in producing the beneficial and therapeutic effects just referred to; there is no evidence at present that such effects are connected with the metabolization of these acids to other substances.

It is particularly to be noted that the beneficial and therapeutic effects of the combination of the two specified acids (or their derivatives) may be adversely effected by the presence of an oily carrier or diluent which comprises at least one member of the group consisting of $C_{8-18}$ saturated fatty acids, oleic acid and derivatives of these acids, and the invention thus excludes the use of such diluents or carriers. As persons skilled in the art will be aware, the use of natural oily diluents and carriers of vegetable or animal origin is accordingly excluded from the scope of the invention.

SUMMARY OF THE INVENTION

The present invention accordingly provides a composition of matter which consists of (a) from about 13.0 to about 27.5% by weight of a compound selected from linolenic acid and derivatives thereof, calculated as the free acid, the derivatives of linolenic acid being both physiologically hydrolyzable and pharmacologically acceptable, and (b) about 87.0 to about 72.5% by weight of a compound selected from linoleic acid and derivatives thereof, calculated as the free acid, the derivatives of linoleic acid being both physiologically hydrolyzable and pharmacologically acceptable.

The present invention also provides, in another aspect, a pharmaceutical formulation which comprises the composition of matter as just defined, together with at least one pharmaceutically acceptable substance selected from diluents, carriers and adjuvants, excluding an oily carrier or diluent which comprises at least one member of the group consisting of $C_{8-18}$ saturated fatty acids, oleic acid and derivatives of these acids.

In yet another aspect, the invention provides a nutritional composition, adapted for consumption by mammals, characterized by the presence of (i) an orally ingestible diluent or carrier, excluding an oily carrier or diluent which comprises at least one member of the group consisting of $C_{8-18}$ saturated fatty acids, oleic acid and derivatives of these acids, (ii) at least one compound selected from linolenic acid and physiologically non-deleterious and hydrolyzable derivatives thereof and (iii) at least one compound selected from linoleic acid and physiologically non-deleterious and hydrolyzable derivatives thereof, such that the proportion of ingredient (ii) calculated as a percentage by weight of the combined ingredients (ii) and (iii) is from about 13.0 to about 27.5%, each of (ii) and (iii) being calculated as free acids.

In still another aspect, there is provided by the invention a method for treating a mammal for the purpose of inducing in the mammal a beneficial effect selected from memory enhancement, analgesia, sleep regulation and inhibition of the symptome of senility which comprises administering to the mammal a composition of matter as defined above in an amount effective to induce the at least one physiological effect, or a pharmaceutical formulation as defined above which contains an amount of the composition of matter effective to induce the at least one physiological effect. It will be appreciated that the compositions and formulations of the invention are intended in particular for administration to humans, or for human consumption, for the purpose of inducing in humans at least one of the aforementioned beneficial effects.

In a further aspect, the invention provides a method for treating Alzheimer's disease and related dementias, and epilepsy, which comprises administering to a person having the symptoms of Alzheimer's disease or related dementias, or to a person susceptible to epilepsy, a symptom-alleviating amount of a composition of matter or pharmaceutical formulation as defined above.

It will be apparent that the methods of the invention may utilize the nutritional compositions as described and claimed herein, which contain either an amount of the composition of matter effective to induce the at least one physiological effect, or a symptom-alleviating effective amount of the composition of matter (in the case of treating Alzheimer's disease or related dementias, or epilepsy), as the case may be.

With regard to the method of the invention as applied to the treatment of epilepsy, it should be noted that for purposes of definition, such terms as "method for the treatment of epilepsy", "alleviation of symptoms", and similar expressions, where used in the present specification and claims, are intended to include inter alia any such treatment which is effective to reduce the incidence and/or intensity of epileptic occurrences in subjects susceptible to such occurrences.

DETAILED DESCRIPTION OF THE INVENTION

The composition of matter according to the invention preferably consists of from about 14.3 to about 25.0% by weight of component (a) and about 85.7 to about 75.0% by weight of component (b), more preferably from about 16.3 to about 24.4% by weight of component (a) and about 83.7 to about 75.6% by weight of component (b).

In accordance with a particular embodiment of the invention, a special memory enhancement effect has been noted when the composition of matter consists of from about 20.0 to about 24.4% by weight of component (a) and about 80.0 to about 75.6% by weight of component (b), or from about 18.2 to about 22.2% by weight of component (a) and about 81.8 to about 77.8% by weight of component (b); and particularly when the composition consists of either about 22.2% by weight of component (a) and about 77.8% by weight of component (b), or about 20.0% by weight of component (a) and about 80.0% by weight of component (b).

As regards the method according to the invention treating Alzheimer's disease and related dementias, and epilepsy, the composition of matter useful therein preferably consists of from about 15.0 to about 24.5% by weight of component (a) and about 85.0 to about 75.5% by weight of component (b), more preferably from about 16.7 to about 22.2% by weight of component (a) and about 83.3 to about 77.6% by weight of component (b), and it is especially preferred to use such a composition of matter which consists of about 19.0% by weight of component (a) and about 81.0% by weight of component (b).

The preferred percentage proportions by weight are also of course applicable to the relationship between the at least one compound selected from linolenic acid and physiologically non-deleterious and hydrolyzable derivatives thereof, and the at least one compound selected from linoleic acid and physiologically non-deleterious and hydrolyzable derivatives thereof (calculated as the free acids), in the nutritional compositions of the invention.

Since, as has been intimated above, it is believed that the combination of linoleic and linolenic acids is the active principle per se which induces the effects mentioned, it will be appreciated by those skilled in the art that instead of the acids themselves, there may be utilized in the composition of the invention derivatives of these acids which are both physiologically hydrolyzable (to the corresponding acids) and pharmacologically acceptable. Such derivatives may for example be selected from salts, esters and amides of the respective acids.

Among suitable salts there may be mentioned the ammonium, sodium, potassium, calcium and magnesium salts as salts with substituted mono- and di-substituted amines and the analogous saturated heterocyclic compounds containing an NH group in the ring, so long as the amines and the analogues in question are physiologically acceptable. As suitable esters there may be mentioned, for example, the ethyl and glyceryl esters. Amides of the acids may also be utilized, e.g. amides of the acids with substituted mono- and di-substituted amines and with the analogous saturated heterocyclic compounds containing an NH group in the ring, so long as the amines and the analogues in question are physiologically acceptable. It will be appreciated that the latter stipulation is necessary (in the case of the amine salts, the amides and their heterocyclic analogues) since it is to be expected that such derivatives will metabolize in the body to the desired acids and the starting amines or heterocyclic compounds. It will of course be evident to a person skilled in the art how to select a particular salt, ester or amide, so as to comply with the requirements of physiologically hydrolyzing to the corresponding acids, and pharmacological acceptability.

The pharmaceutical formulation provided in accordance with the present invention may be adapted for oral, parenteral or rectal administration, and it may be in the form of dosage units. The diluents, carriers and adjuvants are those conventionally used in pharmaceutical and veterinary formulation.

For oral administration, the pharmaceutical formulations of the invention may be utilized as e.g. tablets, capsules, emulsions, solutions, syrups or suspensions. For parenteral administration, the formulations may be utilized as ampoules, or otherwise as suspensions, solutions or emulsions in aqueous or oily vehicles. The need for suspending, stabilizing and/or dispersing agents will of course take account of the fact of the solubility or otherwise of the linoleic and linolenic acids, or of their derivatives used in the formulations, in the vehicles which are used in particular embodiments. Thus, for example, where the acids themselves are used, account will be taken of the fact that these have a relatively low water solubility and in general a relatively high oil solubility. The formulations may additionally contain e.g. physiologically compatible preservatives and antioxidants.

The pharmaceutical formulations of the invention may also be utilized as suppositories with conventional suppository bases such as cocoa butter or other glycerides. As is well known in the pharmaceutical art, the formulations may also be made available in a depot form which will release the active composition slowly in the body, over a preselected time period.

The nutritional composition according to the invention includes as a necessary component an orally ingestible diluent or carrier; this may for example comprise a substance selected from sugar-based confectionery, a manufactured cereal, a fruit or vegetable product, a beverage or beverage concentrate, or any inert diluent, carrier or excipient known in the pharmaceutical art. It is intended generally that ingredients (ii) and (iii), as previously defined, may be used in nutritional compositions in any of the forms in which these are known and practiced in the art. Thus, the nutritional compositions may take the form of, e.g., sugar-based confectionery such as candies or chocalate, breakfast cereals, fruit or vegetable purees or beverages, other beverages (including those based on carbonated water), or beverage concentrates generally (including those in the form of e.g. powders, granules, flakes or crystals, which are intended to be mixed with hot or cold water and/or milk). The nutritional compositions may also generally be in the form of powders, tablets, capsules, solutions, concentrates, syrups, suspensions, gels or dispersions. It will be evident that when the nutritional compositions take the form of dispersions or suspensions, it will usually be necessary to use an acceptable (i.e. non-toxic and otherwise suitable) dispersing or suspending agent, as is well known in the nutritional and pharmaceutical arts. When these compositions are utilized in the form of capsules, it will be evident that gelatin or other known suitable ingestible materials may be used for encapsulation.

The present invention moreover includes the nutritional compositions described herein, which are adapted for consumption by non-human, as well as human mammals.

The present invention further includes nutritional compositions which also include any of the known vitamins. Thus for example, such compositions (which may be, but need not be, in the form of aqueous suspensions) may comprise at least one water-soluble vitamin selected from thiamine, riboflavin, niacin, pyridoxine, pantothenic acid, biotin, folic acid, cobalamin and ascorbic acid. Alternatively or additionally, such compositions may comprise at least one oil-soluble vitamin selected from retinol, calciferol, tocopherol and menadione. The nutritional compositions of the present invention may also comprise in combined form at least one element selected from sodium, potassium, calcium, phosphorus, magnesium, chlorine and sulfur, and additionally or alternatively, at least one element selected from iron, copper, iodine, manganese, cobalt, zinc, molybdenum, fluorine, selenium and chromium. These compositions may also contain other natural or synthetic antioxidants.

The nutritional compositions of the present invention may also comprise other unsaturated fatty acids, such as for example those known to be metabolized in the body to prostaglandins, e.g. dihomo-gamma-linolenic acid, arachidonic and eicosapentaenoic acids, as well as physiologically compatible derivatives thereof, such as salts, esters and amides of such acids.

The invention will be illustrated by the following Examples.

EXAMPLE I

TREATMENT OF EXPERIMENTAL ANIMALS

METHOD

Subjects were male Long Evans (hooded) rats weighing initially 100 g. They were housed individually in hanging stainless steel, wire-mesh cages in a well-ventilated room at an ambient temperature of 20°-22° C. Light (Vita-Lite, Dura-Test, N.J.) was provided from 06.00 hrs. to 18.00 hrs. daily. A control group of rats (Group A) was fed a diet of linoleic acid 35 mg./kg. diet plus linolenic acid 0.15 mg./kg. diet. Other groups of rats received the same diet, plus a daily aqueous injection of a mixture of linoleic and linolenic acids (with polyethylene glycol emulsifier), each rat receiving by injection 25 mg. linolenic acid, the balance being linoleic acid. (It will be appreciated that the amounts of linoleic and linolenic acids ingested by the rats from the diet just described is insignificant compared with the amounts of these substances administered by injection.) The composition of the injected unsaturated fatty acid mixture was varied among different experimental groups; the percentage by weight of linolenic acid in the mixture was as follows (balance linoleic acid): 25.0; 22.2; 20.0; 18.2; 16.7; 15.4; and 14.3 (these groups were respectively labelled B, C, D, E, F, G and H. Otherwise expressed, the ratios by weight were respectively; 1:3; 1:3.5; 1:4; 1:4.5; 1:5; 1:5.5; and 1:6.0. Another route of administration (i.e., supplemented water or an enriched diet) was tested with closely similar results. Throughout the experiment the rate had free access to food and water. Handling of the rats was kept to a minimum, so as not to interfere with the learning.

Every week groups of rats, from each treatment regimen, were tested in the learning apparatus. The level of motor activity, pain threshold, colonic temperature and d-amphetamine-induced hypothemis were tested in different groups. The order of testing was as follows: first day, rotor activity; second day, pain threshold; third day, thermoregulation.

The learning apparatus is known from the scientific literature. Briefly, a circular tank (110 cm. in diameter) was filled with water (at the 40 cm. level), which was made opaque by the addition of powdered milk, so that rats swimming in the tank were unable to see an escape platform (7.5 cm. in diameter) submerged 2 cm. below the water level. Each animal was released facing the wall in one of four predetermined starting points located every 90° around the inner perimeter. A mass-learning technique was used, and each rat was tested 8 times per day in the tanks. The order of starting points was randomly predetermined. Each rat was allowed 120 seconds to find the platform, and intertrial interval was 20 seconds. The rate were tested during 3 consecutive days. During this period the platform was in the same location in the tank. After completion of the session on day 3, the platform was removed to another location in the tank, and the performance of rats in the new position was recorded. For each of the 24 trials (8 trials × 3 days) the latency to reach the platform was recorded. A cut-off point criterion (i.e., the first trial to reach latency of 10 seconds, without increasing the latency in a later trial) was used to calculate the learning capacity of each diet group. To calculate the resistance to extinction, the time which the rats spent in the "old position" in the first trial was recorded.

The level of motor activity was assessed in an open field apparatus by recording the number of horizontal movements (infrared photobeam crossing) and rearing movements (determined from videotapings) made during the 15 minute sessions. The apparatus was very similar to the one previously described by Coscina et al. in 1986.

Pain threshold was measured with a hot plate (60 × 60 cm.) heated by a thermostatic bath (Hakke, Germany) to 58 +/− 0.20 C. The latency to lick the paw was recorded to the nearest 0.1 second. On the third day, the basic colonic temperature of each rat was measured (YSI telethermometer, model 43TA, Yellow Springs, Ohio). The rat was then injected with 15.0 mg./kg., i.p., d-amphetamine and placed immediately into a 4° C. cold room for 1 hour.

All tests were conducted between 10.00 and 14.00 hrs. There were 9 rats in each experimental group. At the end of each week of the experiment, the brain of the rate was removed for biochemical analysis for a different study. All experiments were conducted "double blind," i.e., the experimenter was unaware of the diet fed to the individual subjects or which treatment the rat received. Comparisons across diets and weeks of treatment were analyzed by analysis of variance with contrast tests.

RESULTS

TABLE 1

| GROUP | NUTRITIONAL FACTORS | |
|---|---|---|
| | FOOD INTAKE (K Cal) | WEIGHT GAIN |
| A | 2565 +/− 39 | 237 +/− 4.7 |
| B | 2575 +/− 80 | 230 +/− 7.0 |
| C | 2545 +/− 75 | 235 +/− 2.8 |
| D | 2534 +/− 68 | 237 +/− 4.6 |
| E | 2543 +/− 72 | 239 +/− 6.1 |
| F | 2562 +/− 57 | 235 +/− 3.3 |
| G | 2586 +/− 48 | 238 +/− 3.9 |
| H | 2533 +/− 61 | 234 +/− 5.5 |
| | Data expressed as M +/− SEM | |
| P | N.S. | N.S. |

Unsaturated fatty acid treatment has no effect on either the amount of food intake (in kCal. units) nor on the rate of body weight gain.

LEARNING

TABLE 2

| | NUMBER OF TRIALS TO REACH CRITERION (10 secs.) | | | | |
|---|---|---|---|---|---|
| | WEEKS OF TREATMENT | | | | |
| GROUP (P) | 0 | 1 | 2 | 3 | 4 |
| A (N.S.) | 19.6 +/− 3.3 | 19.0 +/− 3.7 | 20.3 +/− 2.5 | 18.5 +/− 2.9 | 19.1 +/− 2.7 |
| B (N.S.) | 20.1 +/− 4.1 | 18.0 +/− 4.0 | 19.9 +/− 4.5 | 17.1 +/− 4.0 | 17.0 +/− 3.2 |
| C (0.01) | 17.1 +/− 3.3 | 12.5 +/− 2.1* | 10.7 +/− 4.1* | 7.9 +/− 3.9* | 5.6 +/− 2.5* |
| D (0.001) | 18.5 +/− 2.0 | 9.3 +/− 2.6* | 7.1 +/− 2.9* | 6.1 +/− 2.8* | 6.1 +/− 2.5* |
| E (0.01) | 19.1 +/− 2.3 | 14.2 +/− 3.7* | 12.8 +/− 3.9* | 9.6 +/− 3.0* | 9.0 +/− 3.4* |
| F (0.01) | 19.5 +/− 3.5 | 16.1 +/− 2.6 | 11.2 +/− 1.1* | 9.2 +/− 1.8* | 7.9 +/− 1.0* |
| G (N.S.) | 19.7 +/− 3.8 | 18.1 +/− 3.3 | 18.4 +/− 2.9 | 17.9 +/− 4.1 | 18.6 +/− 2.6 |
| H (N.S.) | 21.0 +/− 4.0 | 20.0 +/− 3.0 | 19.6 +/− 3.1 | 18.8 +/− 3.9 | 19.1 +/− 3.0 |
| P | N.S. | 0.01 | 0.01 | 0.01 | 0.01 |

*Statistically differs from Control (M +/− SEM)

Treatment with the ratios 1:3.5 to 1:5 (Groups C to F) has a significant effect on the rate of learning. The optimal ratio was 1:4 (Group D).

Comparative experiments were carried out by administering, in place of the inventive compositions, eleven similar non-inventive compositions comprising (i) 100% linolenic, linoleic or gamma-linolenic soids, respectively, or (ii) 95.2, 90.9, 83.3, 50.0, 9.1, 6.3, 4.8, or 3.8 linolenic acid (balance linoleic acid). After 4 weeks, the results in these cases generally showed either no significent change in learning ability, or a tendency to detract from learning ability; in two cases (9.1 and 6.3) an initial apparent small increase in learning ability had diminished by the end of 4 weeks.

TABLE 3
TIME IN THE 'WRONG' LOCATION; MEANS OF THE FIRST 2 TRIALS

| GROUP (P) | WEEKS OF TREATMENT | | | | |
|---|---|---|---|---|---|
| | 0 | 1 | 2 | 3 | 4 |
| A (N.S.) | 22.9 +/− 3 | 24.3 +/− 4 | 19.0 +/− 3 | 22.3 +/− .4 | 25.1 +/− 4 |
| B (N.S.) | 18.5 +/− 3 | 19.4 +/− 4 | 20.6 +/− 6 | 20.6 +/− 4 | 20.1 +/− .5 |
| C (0.001) | 20.3 +/− 4 | 30.9 +/− 2* | 35.3 +/− 4* | 39.2 +/− 4* | 49.4 +/− 3* |
| D (0.01) | 19.5 +/− 3 | 24.1 +/− 3 | 29.3 +/− 4* | 36.6 +/− 4* | 39.1 +/− 4* |
| E (0.01) | 20.8 +/− 4 | 25.1 +/− 4 | 30.1 +/− 3* | 33.1 +/− 4* | 36.1 +/− 5* |
| F (0.01) | 19.4 +/− 3 | 22.1 +/− 3 | 29.1 +/− 5* | 30.1 +/− 5* | 32.2 +/− 5* |
| G (N.S.) | 22.8 +/− 4 | 19.4 +/− 3 | 19.0 +/− 3 | 19.6 +/− 4 | 18.1 +/− 4 |
| H (N.S.) | 19.1 +/− 5 | 18.7 +/− 5 | 19.9 +/− 4 | 21.1 +/− 3 | 19.6 +/− 5 |
| P | N.S. | 0.01 | 0.001 | 0.001 | 0.001 |

*Statistically differs from Control (M +/− SEM).

Unsaturated fatty acid treatment with ratios of 1:3.5–1:5 (Groups C to F) has a significant effect on retention of the old learning. The most effective ratio was 1:3.5 (Group C).

MOTOR ACTIVITY

TABLE 4
AT THE END OF THE 4 WEEKS' TREATMENT

| GROUP | LINE CROSSING | REARING |
|---|---|---|
| A | 76.0 +/− 27 | 75.0 +/− 5.0 |
| B | 74.0 +/− 30 | 75.5 +/− 5.5 |
| C | 70.7 +/− 25 | 76.0 +/− 4.5 |
| D | 70.3 +/− 33 | 84.3 +/− 5.5 |

TABLE 4-continued
AT THE END OF THE 4 WEEKS' TREATMENT

| GROUP | LINE CROSSING | REARING |
|---|---|---|
| E | 72.1 +/− 29 | 77.7 +/− 6.6 |
| F | 74.1 +/− 32 | 74.6 +/− 5.1 |
| G | 72.5 +/− 25 | 76.9 +/− 6.1 |
| H | 75.5 +/− 31 | 80.0 +/− 5.5 |
| P | N.S. | N.S. |

None of the treatment has any effect on horizontal or on vertical movement.

PAIN THRESHOLD

TABLE 5

| GROUP (P) | WEEKS OF TREATMENT | | | | |
|---|---|---|---|---|---|
| | 0 | 1 | 2 | 3 | 4 |
| A (N.S.) | 7.9 +/− .9 | 7.8 +/− .8 | 8.0 +/− .6 | 7.9 +/− .9 | 8.1 +/− .9 |
| B (N.S.) | 8.0 +/− .8 | 7.9 +/− .7 | 8.0 +/− .9 | 8.1 +/− .7 | 7.8 +/− .7 |
| C (0.01) | 7.8 +/− .6 | 11.9 +/− .7 | 13.9 +/− .7* | 16.5 +/− .6* | 20.1 +/− 1.1* |
| D (0.01) | 8.1 +/− .8 | 12.1 +/− .6* | 14.5 +/− .6* | 18.2 +/− .7* | 21.1 +/− .9* |
| E (0.01) | 7.8 +/− .6 | 9.0 +/− .9* | 9.0 +/− .8* | 14.1 +/− .7* | 17.4 +/− .7* |
| F (0.01) | 8.1 +/− .9 | 9.9 +/− .9 | 11.5 +/− .7 | 14.1 +/− .7* | 16.3 +/− .7* |
| G (N.S.) | 7.6 +/− .7 | 8.0 +/− .3 | 8.8 +/− .8 | 8.0 +/− .8 | 8.1 +/− .9 |
| H (N.S.) | 8.0 +/− .9 | 8.0 +/− .4 | 8.5 +/− .5 | 8.3 +/− .7 | 8.3 +/− .7 |
| P | N.S. | 0.05 | 0.01 | 0.01 | 0.01 |

*Statistically differs from control (M +/− SEM).

Unsaturated fatty acid treatments with ratios of 1:3.5 to 1:4.5 (Groups C to E) cause analgesia among rats which were placed on a hot plate (58° C.). The most effective ratio seems to be 1:4 (Group D).

THERMAL RESPONSE TO D-AMPHETAMINE AT 4° C.

TABLE 6

| GROUP (P) | WEEKS OF TREATMENT | | | | |
|---|---|---|---|---|---|
| | 0 | 1 | 2 | 3 | 4 |
| A (N.S.) | −1.9 +/− .7 | −1.8 +/− .8 | −1.7 +/− .6 | −1.9 +/− .7 | −2.0 +/− .9 |
| B (N.S.) | −1.9 +/− .9 | −1.9 +/− .9 | −1.8 +/− .7 | −2.0 +/− .9 | −2.1 +/− .7 |
| C (0.001) | −2.0 +/− .5 | −.9 +/− .3* | −.8 +/− .3* | +.9 +/− .9* | +1.1 +/− .7* |
| D (0.001) | −2.0 +/− .7 | −.9 +/− .6* | +.9 +/− .5* | +1.1 +/− .7* | +1.2 +/− .6* |
| E (0.001) | −1.9 +/− .8 | −.6 +/− .9* | +.6 +/− .3* | +.9 +/− .9* | +.9 +/− .9* |
| F (0.01) | −1.9 +/− .8 | −.9 +/− .7* | −.9 +/− .7* | +.7 +/− .5* | +1.1 +/− .9* |
| G (N.S.) | −1.9 +/− .9 | −2.0 +/− .7 | −1.8 +/− .7 | −1.8 +/− 1.2 | −1.9 +/− .7 |
| H (N.S.) | −2.0 +/− .9 | −1.9 +/− .7 | −2.1 +/− .9 | −2.0 +/− .9 | −2.2 +/− 1.1 |
| P | N.S. | 0.05 | 0.01 | 0.01 | 0.01 |

*Statistically differs from Control (M +/− SEM)

Unsaturated fatty acid treatment protected rats from d-amphetamine induced hypothermia at ambient temperature of 4° C. A ratio of 1:4 (Group D) seems to be most effective.

SLEEP PARAMETERS

A small number of rats (n=6) received unsaturated fatty acids at a ratio of 1:3.5 (as in Group C) for 4 weeks. At the end of the treatment period the length of total sleeping hours and REM percentage was examined and compared with saline treated rats. A strong tendency (but not statistically significant) of longer sleeping hours (+30%) and an increase in REM periods (+18%) were found in treated rats.

THE EFFECT OF IRON DEFICIENCY ON LEARNING

Iron deficiency induced severe learning deficits both in water maze and in water tank learning. Similar deficits were obtained by brain lesions. While control rats needed 19.6+/−3.3 trial to reach the criterion of learning, iron-deficient rats needed 26.4+/−1.1 to reach the same performance. Iron-deficient rats treated for 3 weeks with 1:4 ratio (as in Group D) before training reached the criterion in 15.9+/−4.8 trial while saline treated rats had the same 27.0+/−1.2 trials to criterion.

THE EFFECT OF AGING ON LEARNING

Old male rats (20-22 months old) showed a strong deficit in learning. Among 7 non-treated rats none was able to learn the swim test. The group of old rats (n=6) was able to learn the swim test after 1:4 ratio treatment (as in Group D) of 6 weeks duration. They learned the task in 15.9+/−6.1 trials. However, due to the small number of rats, and because it is one trial without replication, it is difficult to draw positive conclusions on the effect of such treatment on old age learning deficit.

THE EFFECT OF OTHER FATTY ACID & NATURAL OIL CARRIERS ON LEARNING

When linolenic acid was added to corn oil, olive oil or sunflower oil, or when linoleic acid was added to linseed oil, in order that the linolenic:linoleic acid ratio therein (calculated as free acids) should be 1:4 by weight, such compositions had no effect on learning. Also, when a mixture of free linoleic and linolenic acids in this ratio was mixed with free palmic acid or free stearic acid, as carrier, such compositions had no effect on learning, while substitution of oleic acid for the palmic or stearic acid in these experiments gave inconclusive results.

It is concluded that palmic, stearic and (probably) $C_{8-18}$ saturated fatty acids generally and oleic acid, as well as derivatives thereof, when comprised in carriers or diluents, adversely affect the beneficial properties of the inventive compositions, and also that natural oils are unsuitable for use as carriers or diluents for the compositions of the invention. A person skilled in the art will be able to determine without undue experimentation whether or not smaller than carrier quantities of the thus excluded acids (and their derivatives), would adversely affect the advantageous biological activity of the inventive composition of matter. Insofar as it may be found that these smaller quantities would not unduly affect such activity, compositions including them as well as the inventive combination of linoleic and linolenic acids are deemed to be comprised within spirit and scope of the invention.

EXAMPLE II

STUDY OF HUMANS 225 mg. of the composition of one embodiment of the present invention which contained 22.2% by weight linolenic acid and the balance linoleio acid, was given twice daily to 12 demented geriatric patients (male and female, mean age 76.5+/−2). A comparable group of 12 geriatric patients (similar in age and severity of dementia) was given a placebo (lemonade syrup, the vehicle of the unsaturated fatty acid mixture). The treatment length was 28 days. The study was carried out in double-blind fashion; (however, there were some differences between the treatment and the lemonade, mainly in oclor). The medical staff, doctors and nurses, were instructed to follow the 24 subjects and to tell by the end of the period which one was "improved" on a subjective scale. The medical staff identified correctly 10 of the 12 treated patients as improved, and none of the 11 placebo group (one of the subjects in this group had to leave the experiment because of other medical problems). The patients seemed to be improved in the following aspects: they were more cooperative; they were in a better mood; appetites improved; they were able to remember their way around the hospital, and complained less about sleep disturbances. The food intake (amount and type of food) was not controlled. However, the rate of success in identifying treated subjects was highly significant.

EXAMPLE III

TESTS ON ALZHEIMER'S DISEASE PATIENTS

Example IIIa

Selection of Patients

Alzheimer's disease was defined according to the Diagnostic & Statistical Manual of the American Psychiatrists Association, 3rd Edn., March 1980. The criteria for inclusion are: complaints of discrientation in space and time, cognitive deficits and low scores in the Mini-Mental Test. Criteria for exclusion from the study are: multi infarotion dementia, depressive or post-depressive dementia, post-traumatic dementia, post-psychotic dementia, known endocrine disorder, normintensive hydrocephalus, very aggressive patient, very severe condition requiring constance assistance in the daily routine.

Criteria for Assessment of Results

The guardian was asked to assess the severity of the patient's condition in 12 areas of behaviour on a five-point scale, a score of 5 indicating a severe problem, a score of 1 indicating no problem. The 12 areas were as follows: 1. Space orientation: can the patient find the way to return alone without confusion and without losing sense of direction? 2. Level of cooperation with family and doctors etc. 3. General mood of patient, especially whether aggressive. 4. The patient's appetite, attention to food, time of meals, interest in food. 5. Ability of patient to keep belongings in order and organize his life. 5. Short-term memory—ability to remember recent events. 7. Long-term memory—ability to remember remote events. 8. Sleep habits and sleep disturbances. 9. Whether patient is alert during daytime: periods of alertness and span of attention. 10. Does patient have auditory or visual hallucinations; if so, at what time of day? 11. Is patient capable of self-expression in clear speech and ideas? 12. Control of urination.

Method

Treatment in accordance with the present invention (or placebo) were carried out on 100 patients (79 male and 21 female; 24 of the 100 were hospitalized), of ages in the range 50–73 years. 71 of the patients had been definitely diagnosed as having Alzheimer's disease at least 4 years previously; in the past they had been treated with hydergin, various cholinergic drugs, piracetam or/and lecithin. The present treatment was administered to 60 patients, while 40 received placebo. The following table summarizes the patient sample.

| Classification of Alzheimer's Patients | | | | |
|---|---|---|---|---|
| | Hospitalized | | Non-hospitalized | |
| | M | F | M | F |
| Treatment | 9 | 3 | 40 | 8 |
| Placebo | 9 | 3 | 21 | 7 |
| Totals | 18 | 6 | 61 | 15 |

Patients received oral doses, 1 ml. morning and evening, of either medication or placebo, over a period of three weeks; the medication, which was kept in the cold or refrigerated, comprised per ml. 0.25 ml. of a mixture of linolenic and linoleic acids (Sigma) in a 1:4.25 weight ratio (19.05%: 80.95%), 0.73 ml. paraffin oil, 0.02 ml. alphatocopherol (Vitamin E, Sigma) and a few drops of flavoring (almond essence). At the end of the three-week period, each patient was medically reexamined, PEG recorded and samples of blood and urine were tested. A Mini Mental test was administered and the guardian was again asked to rate the severity of complaints on the basis of the above 12 questions.

Results (1) The following table summarizes scores in the Mini Mental Test. The stated figures are average values for the number of patients (n).

| Treatment of Alzheimer's Patients - Mini Mental Test Scores | | | |
|---|---|---|---|
| | | Treatment (n = 60) | |
| | Placebo (n = 40) | responders (n = 49) | non-responders (n = 11) |
| Before | 7.3 ± 3.1 | 7.8 ± 2.9 | 7.6 ± 3.2 |
| After | 7.5 ± 3.5 | 16.0 ± 3.7* | 8.0 ± 2.5 |

*P<0.01

(2) The following table summarizes the results of assessment of patients' condition in the 12 areas detailed above, on the 5-point scale, before and after treatment. A change of at least 1.4 units is considered significant. Each fraction denotes:

$$\frac{\text{number of patients improved}}{\text{number of patients with severe problem}}$$

| Treatment of Alzheimer's Patients - Ratings in 12 Areas | | | | |
|---|---|---|---|---|
| | Placebo (n = 40) | | Treatment (n = 60) | |
| AREA | fraction improved | % | fraction improved | % |
| 1. Space orientation | 3/33 | 9.0 | 37/50 | 74.0 |
| 2. Cooperativeness | 2/31 | 5.1 | 28/49 | 57.1 |
| 3. Mood | 5/27 | 18.5 | 27/44 | 61.4 |
| 4. Appetite | 2/31 | 5.1 | 26/48 | 54.2 |
| 5. Organization | 4/32 | 12.5 | 33/48 | 68.7 |
| 6. Short-term memory | 1/3— | 2.9 | 40/59 | 74.0 |
| 7. Long-term memory | 0/38 | 0 | 34/58 | 58.7 |
| 8. Sleep problems | −2/27 | −7.4 | 21/29 | 74.4 |
| 9. Daytime alertness | −2/33 | −5.1 | 29/47 | 61.7 |
| 10. Hallucinations | −2/10 | −20.0 | 12/14 | 85.0 |
| 11. Self-expression | 1/36 | 2.7 | 16/52 | 30.7 |
| 12. Bladder control | 3/14 | 21.4 | −2/27 | −7.4 |

(3) General physiological effects

No major side effects were found after the three week treatment period; one patient only suffered from severe stomach upset and diarrhhea. Body temperature and blood pressure (systolic and diastolic) were unchanged at the end of this period. Biochemical blood and urine laboratory tests did not show significant changes after treatment. There was no increase in total lipids in the blood. There was a tendency of the blood cholesterol level to decrease, but this was not necessarily of statistical significance.

Example IIIb

A further group of 13 Alzheimer's Disease out-patients, 5 male and 4 female, in the age range of 59–71 years, was treated with the same oral medication (no placebo), in a similar manner to Example IIIa.

Results (1) The following table summarizes scores in the Mini Mental Test. The stated figures are average values for the number of patients (n).

| Treatment of Alzheimer's Patients - Mini Mental Test Scores | |
|---|---|
| | Treatment (n = 13) responders (n = 10) |
| Before | 7.0 ± 1.7 |
| After | 15.6 ± 2.1* |

*P<0.01

(2) The following table summarizes the results of assessment of patients' condition in the 12 areas detailed above, on the 5-point scale, before and after treatment. A change of at least 1.4 units is considered significant. Each fraction denotes:

$$\frac{\text{number of patients improved}}{\text{number of patients with severe problem}}$$

| Treatment of Alzheimer's Patients - Ratings in 12 Areas | | |
|---|---|---|
| | Treatment (n = 13) | |
| AREA | fraction improved | % |
| 1. Space orientation | 8/12 | 66 |
| 2. Cooperativeness | 5/12 | 42 |
| 3. Mood | 5/9 | 55 |
| 4. Appetite | 6/11 | 55 |
| 5. Organization | 8/11 | 72 |
| 6. Short-term memory | 10/12 | 83 |
| 7. Long-term memory | 9/12 | 75 |
| 8. Sleep problems | 4/6 | 66 |
| 9. Daytime alertness | 5/11 | 45 |

-continued

Treatment of Alzheimer's Patients - Ratings in 12 Areas

| AREA | Treatment (n = 13) fraction improved | % |
|---|---|---|
| 10. Hallucinations | 5/6 | 83 |
| 11. Self-expression | 5/12 | 42 |
| 12. Bladder control | 0/7 | 0 |

Unwanted side effects were not observed in the group of 13 patients. It is seen that the results in Example IIIb are in line with the noted improvement in the condition of Alzheimer's patients found in Example I, when the method according to the present invention is utilized.

EXAMPLE IV

TESTS ON ANIMAL MODELS OF EPILEPSY

Preliminary note

Tests on animal models enable possible antiepileptic drugs to be evaluated for potential therapeutic use in humans. Such tests measure the protection afforded by the drug against the convulsant effects of chemical or electrical stimulants. An important chemical stimulant utilized for these tests is pentylenetetrazol (PTZ, Metrazol-Knoll), which has been used in experimental animals to induce grand mal seizures.

EXAMPLE IVa

The inventive composition (labelled "SR-3") administered to animal models in accordance with the method of the invention comprised per ml. 0.40 ml. of a mixture of linolenic and linoleic acids (Sigma) in a 1:4 weight ratio (20%:80%), 0.59 rl. paraffin oil, and 0.01 ml. alpha-tocopherol (Vitamin E, Sigma).

In a first stage, the $ED_{50}$ for PTZ-induced grand mal seizures in SPD rats was investigated and found to be 76.5 mg./kg. The $LD_{50}$ is tightly closed at 81.0 mg./kg.

In a second stage, 80 (150 g.) male rats were divided into two groups. One group received 0.2 ml. i.p. saline treatment daily (4C rats) and the other group received treatment with 0.2 ml. i.p. SR-3 daily (40 rats), for a period of three weeks. After the three-week treatment, the rats were given one of two doses of PTZ, 50 mg./kg. or 100 mg./kg. The rats were observed by two independent observers, who were ignorant of which treatment each rat received. An EEG recording was not performed. The following variables were recorded in Table 7, below:

1. latency (seconds) to the first grand mal seizure (tonic-clonic contractions of the limbs, trunk and head, falling, saliva and blood discharge from the mouth);
2. number of rats responding with grand mal seizures;
3. mean duration (in seconds) of the grand mal seizures;
4. number of rats that died not exhibiting grand mal seizures but showing "infantile spasms" (sudden flexion of the forelegs, forward flexion of the trunk, or extension of the rear legs), the attack lasting only a few seconds, but it was repeated several times;
5. number of rats that died 15 minutes after PTZ injection.

TABLE 7

Study of the effect of SR-3 on animal modesl of PTZ-induced epilepsy

| Pretreatment | PTZ dose (mg./kg.) | Variable studied | | | | |
|---|---|---|---|---|---|---|
| | | 1 | 2 | 3 | 4 | 5 |
| Saline* | 50 | 28 ± 12 | 8 | 637 ± 31 | 8 | 9 |
| SR-3* | 50 | 252 ± 11 | 1 | 24 | 1 | 0 |
| Saline* | 100 | 7 ± 3 | 19 | 893 ± 14 | 1 | 20 |
| SR-3* | 100 | 154 ± 25 | 3 | 27 ± 6 | 4 | 2 |

*number of rats in each group = 20

The results clearly showed that pretreatment in accordance with the invention protected the rats from grand mal seizures induced by PTZ. Most of the rats (19/20) receiving the placebo that were challenged with 100 mg./kg. PTZ exhibited clear out grand mal seizures. It is of interest to note that the seizure began shortly after the PTZ injection, and lasted for about 15 minutes without interruption, until death occurred. All of these rats were dead 15 minutes after the PTZ injection. In contrast, rats pretreated with SR-3 and later challenged with 100 mg./kg. PTZ were very much protected. Only 3 out of 20 of this group showed grand mal seizures, and even in these 3 cases the attacks lasted only about 25 seconds; only 2 of the rats exhibiting seizures were dead 15 minutes after the PTZ injection. Another 12 rats from this group were found dead 4 hours after the PTZ injection.

Similar SR-3 protection was found in the group receiving the smaller dose. In the rats receiving saline solution, 8 out of the 20 had grand mal seizures with a latency of about 0.5 minute. The duration of the attacks was shorter than in the group receiving the larger PTZ dose. Only one rat from the SR-3 group showed a brief grand mal attack. In the group receiving the placebo, 9 rats were dead 15 minutes after the PTZ injection. No immediate deaths occurred in the SR-3 group and only 3 rats in this group were found dead 4 hours later; all others recovered.

EXAMPLE IVb

The use of ferrous or ferric salts injected into the cortex or amygdala-hippocampus complex for the induction of epileptogenic discharge (epileptic foci) is well-known. A group of 50 SPD male rats were prepared for this experiment by implantation of canules in their brain. The tip of the canules was in the amygdala according to Czennansky et al (Life Sciences, 1988, 32: 385-390). Then, 25 rats received SR-3 in daily injections as in Example IVa. The other 25 rats received a daily injection of saline (0.9% NaCl). After 3 weeks of treatment, all rats received 100 ^[f^/M $FeCl_3$ intraventicularly through the canules into the amygdala. Only 2 out of 25 rats which were treated with saline did not exhibit epileptic seizure, while 21 of the 25 rats pretreated with SR-3 were protected from $FeCl_3$-induced epileptic seizures.

EXAMPLE IVc

In this method of investigation according to Craig, C. R. and Colasanti, B. J., 1989 Pharmacol. Biochem Behav. 31: 667-70, PTZ was used to induce seizure and the ability of SR-3 to protect from seizure was examined. 15.0 mg./kg. was injected every 15 minutes until seizure occurred. For this purpose, seizure is defined as a single episode of colonic spasms of both forelimbs and hindlimbs lasting at least 5 secs., followed by loss of righting reflex. The results in the following table are expressed as the number of periods to seizure (mean + S.D.; ANOVA = $P<0.001$).

|  | First Week | Second Week | Third Week |
|---|---|---|---|
| Control (n = 25) | 4.32 ± 1.30 | 3.72 ± 1.41 | 3.50 ± 1.80 |
| SR-3 (n = 25) | 18.64 ± 3.09 | 19.94 ± 3.21 | 22.75 ± 3.45 |
| p< | 0.001 | 0.001 | 0.001 |

The above results show that SR-3 afforded clear protection, insofar as many more injections of PTZ were needed to evoke seizure in the SR-3 group than in the control group, with no apparent habituation from one week to another.

EXAMPLE IVd

In this model, 55 non-audiogenic rate were made audiogenic (i.e. they are responsive with seizure to auditory stimuli) by chronic administration of p-cresol over a 7-week period; the effect of p-cresol lasts 4–5 weeks (see Yehuda, S. et al, 1577 Internat. J. Neurcsci. 7: 223-6). Then, 27 rats were treated with saline and 28 rats received SR-3, after which all rats were subjected to the same auditory stimuli and observed for 4 hours. Seizure were observed in 23 out of the 27 control rats, but in only 6 out of the 28 SR-3 treated rats.

The overall results in Example IV indicates that the composition of the invention affords protection from seizures even when the animals under investigation were already seizure-prone.

While the present invention has been particularly described with reference to certain embodiments, it will be apparent to those skilled in the art that many modifications and variations may be made. The invention is accordingly not to be construed as limited in any way by such embodiments, rather its concept is to be understood according to the spirit and scope of the claims which follow.

I claim:

1. A method for treating a mammal for the purpose of inducing therein at least one physiological effect selected from memory enhancement and analgesia, which comprises administering to the mammal, in absence of an oily carrier or diluent which comprises at least one member of the group consisting of $C_{8-18}$ saturated fatty acids, oleic acid and derivatives of these acids, a composition of matter which consists of (a) from about 16.7 to about 22.2% by weight of at least one compound selected from the group consisting of linolenic acid and salts, esters, and amides thereof, calculated as the free acid, said salts, esters, and amides of linolenic acid being both physiologically hydrolyzable and pharmacologically acceptable, and (b) about 83.3 to about 77.8% by weight of at least one compound selected from the group consisting of linoleic acid and salts, esters, and amides thereof, calculated as the free acid, said salts, esters, and amides of linoleic acid being both physiologically hydrolyzable and pharmacologically acceptable, said composition of matter being administered in an amount effective to induce said at least one physiological effect, provided that when said salts of linolenic and linoleic acids are metal salts of these acids, then the metal is selected from the group consisting of sodium, potassium, calcium and magnesium.

2. A method according to claim 1, wherein said composition of matter consists of substantially 20.0% by weight of component (a), balance to make 100% component (b).

3. A method according to claim 1, wherein said composition of matter consists of substantially 22.2% by weight of component (a), balance to make 100% component (b).

4. A method for treating a mammal for the purpose of inducing therein at least one physiological effect selected from memory enhancement and analgesia, which comprises administering to the mammal a pharmaceutical formulation which comprises:

a composition of matter which consists of from 16.7 to 22.25 by weight of at least one compound selected from the group consisting of linolenic acid and salts, esters, and amides thereof, calculated as the free acid, said salts, esters, and amides of linolenic acid being both physiologically hydrolyzable and pharmacologically acceptable, and 83.3 to 77.8% by weight of at least one compound selected from the group consisting of linoleic acid and salts, esters, and amides thereof, calculated as the free acid, said salts, esters, and amides of linoleic acid being both physiologically hydrolyzable and pharmacologically acceptable, in combination with at least one pharmaceutically acceptable substance selected from the group consisting of diluents, carriers and adjuvants except an oily carrier or diluent which comprises at least one member of the group consisting of $C_{8-18}$ saturated fatty acids, oleic acid and derivatives of these acids, said formulation containing an amount of said composition of matter effective to induce said at least one physiological effect, provided that when said salts of linolenic and linoleic acids are metal salts of these acids, then the metal is selected from the group consisting of sodium, potassium, calcium and magnesium.

5. A method according to claim 4, wherein said composition of matter consists of substantially 20.0% by weight of component (a), balance to make 100% component (b).

6. A method according to claim 4, wherein said composition of matter consists of substantially 22.2% by weight of component (a), balance to make 100% component (b).

7. A method for treating a mammal for the purpose of inducing therein at least one physiological effect selected from memory enhancement, and analgesia which comprises administering to the mammal a composition of matter according to claim 1, in an amount effective to induce said at least one physiological effect.

8. A method according to claim 7, wherein said composition of matter consists of substantially 20.0% by weight of component (a), balance to make 100% component (b).

9. A method according to claim 7, wherein said composition of matter consists of substantially 22.2% by weight of component (a), balance to make 100% component (b).

* * * * *